United States Patent
Han et al.

(10) Patent No.: US 9,523,813 B2
(45) Date of Patent: Dec. 20, 2016

(54) OPTICAL FIBER HAVING A CLADDING LAYER DOPED WITH METAL NANO-PARTICLES, CORELESS OPTICAL FIBER, AND METHOD FOR MANUFACTURING SAME

(75) Inventors: Won Taek Han, Gwangju (KR); Seongmin Ju, Gwangju (KR)

(73) Assignee: GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 0 days.

(21) Appl. No.: 13/979,519

(22) PCT Filed: Apr. 18, 2011

(86) PCT No.: PCT/KR2011/002754
§ 371 (c)(1),
(2), (4) Date: Jul. 12, 2013

(87) PCT Pub. No.: WO2012/096427
PCT Pub. Date: Jul. 19, 2012

(65) Prior Publication Data
US 2013/0287355 A1    Oct. 31, 2013

(30) Foreign Application Priority Data
Jan. 14, 2011    (KR) .................. 10-2011-0003806

(51) Int. Cl.
| G02B 6/00 | (2006.01) |
| G02B 6/02 | (2006.01) |
| C03B 37/023 | (2006.01) |
| G01N 21/552 | (2014.01) |
| G02B 6/122 | (2006.01) |
| B82Y 20/00 | (2011.01) |

(52) U.S. Cl.
CPC .......... *G02B 6/0229* (2013.01); *G01N 21/554* (2013.01); *G02B 6/1226* (2013.01); *B82Y 20/00* (2013.01)

(58) Field of Classification Search
CPC ..... G02B 6/0229; G02B 6/1226; H01S 3/169; G01N 21/554
USPC ...................... 385/12, 123, 126–128; 65/385
See application file for complete search history.

(56) References Cited

U.S. PATENT DOCUMENTS

| 4,608,344 A * | 8/1986 | Carter et al. .................... 436/34 |
| 6,590,647 B2 * | 7/2003 | Stephenson .................... 356/301 |
| 8,072,606 B2 * | 12/2011 | Chau .................... G01N 21/554 356/445 |

(Continued)

FOREIGN PATENT DOCUMENTS

| KR | 10-2008-0061036 | * | 7/2008 | .............. G02B 6/00 |
| NL | EP2187486 A1 | * | 11/2008 | ............. H01S 3/067 |
| WO | WO2004/053552 A1 | * | 6/2004 | .............. G02B 6/25 |

OTHER PUBLICATIONS

PhD thesis "Development and characterization of polysiloxane films for use in optical sensor technology" by Plett, 2008.*

(Continued)

*Primary Examiner* — Robert Tavlykaev
(74) *Attorney, Agent, or Firm* — Hauptman Ham, LLP

(57) ABSTRACT

The present invention relates to an optical fiber for an SPR sensor, characterized in that the optical fiber is comprised of a core layer and a cladding layer surrounding the core layer, and the cladding layer is doped with metal nanoparticles.

16 Claims, 10 Drawing Sheets

(56) References Cited

U.S. PATENT DOCUMENTS

| | | | |
|---|---|---|---|
| 8,467,123 B2* | 6/2013 | Regnier | B82Y 20/00 359/341.5 |
| 2005/0018274 A1* | 1/2005 | Halas et al. | 359/296 |
| 2007/0109544 A1* | 5/2007 | Chau | G01N 21/554 356/445 |
| 2007/0194693 A1* | 8/2007 | Saito et al. | 313/503 |
| 2009/0207486 A1* | 8/2009 | Burov et al. | 359/341.5 |
| 2009/0238216 A1* | 9/2009 | Okada | 372/6 |
| 2010/0203649 A1* | 8/2010 | Thrier | 436/127 |
| 2011/0090506 A1* | 4/2011 | Chau | G01N 21/554 356/445 |

OTHER PUBLICATIONS

"The application of a light guiding flexible tubular waveguide in evanescent wave absorption optical sensing" by Tao et al, Sensors and Actuators, B 120, pp. 724-731, 2007.*

Seongmin Ju et al., Development of Optical Fiber Incorporated with Au Nano—Particles in Cladding Region for Surface Plasmon Resonance Sensor Applications, The Korea Ceramic Conference 2010, Oct. 21, 2010, Jeju, South Korea.

* cited by examiner

OPTICAL FIBER HAVING A CLADDING LAYER DOPED WITH METAL NANO-PARTICLES, CORELESS OPTICAL FIBER, AND METHOD FOR MANUFACTURING SAME

TECHNICAL FIELD

The present invention relates to an optical fiber having a cladding layer doped with metal nano-particles, a coreless optical fiber, and a method for manufacturing the same.

BACKGROUND ART

An optical fiber sensor has rapid response characteristics, high reliability, and a small size, and is not affected by magnetic and electric fields around the optical fiber sensor, thereby making it possible to perform accurate diagnosis and measurement. Due to these advantages, the optical fiber sensor has been applied to a technology for sensing a temperature, pressure, a chemical, displacement, current, or the like.

Particularly, as an optical fiber sensor using a surface plasmon resonance (SPR) phenomenon by a reaction between a surface of the optical fiber and surrounding environment, a gas sensor, a chemical sensor, and a bio sensor, and the like, have been in the spotlight. To this end, a technology of polishing a surface of the optical fiber, a technology of coating the optical fiber, and the like, have been applied.

Generally, the surface plasmon resonance phenomenon is a property generated by the photo-electromagnetic effect. That is, the case in which light having a specific wavelength is irradiated, a resonance phenomenon that light energy is transferred to free electrons is generated in a surface of metal nano-particles.

In the case of the optical fiber sensor using the surface plasmon resonance phenomenon according to the related art, since an optical fiber is manufactured and then metal nano-particles are deposited on a surface of the optical fiber to thereby be utilized as a sensing probe, there is a disadvantage in that secondary processing processes of the optical fiber such as a polishing process, a tapering process, a grating process, and a coating process of the optical fiber are demanded.

DISCLOSURE

Technical Problem

The present invention has been made in an effort to provide an optical fiber capable of being used as a surface plasmon resonance (SPR) sensor without being subjected to a secondary processing process such as a polishing process, a tapering process, a grating process, and a coating process, and a method for manufacturing the same.

Technical Solution

According to a preferred embodiment of the present invention, there is provided an optical fiber for a surface plasmon resonance (SPR) sensor including: a core layer; and a cladding layer enclosing the core layer, wherein the cladding layer is doped with metal nano-particles, and preferably, at least some of the metal nano-particles are exposed to the outside.

Preferably, the cladding layer may be coated with a polymer having a refractive index lower than that of the cladding layer.

Preferably, the metal may be any one selected from a group consisting of gold (Au), silver (Ag), and copper (Cu).

According to another preferred embodiment of the present invention, there is provided a method for manufacturing an optical fiber for an SPR sensor, the method including:

depositing a cladding layer in a quartz glass pipe and partially sintering the deposited cladding layer;

doping the partially sintered cladding layer with metal nano-particles;

drying and sintering the cladding layer doped with the metal nano-particles;

forming a core layer on the cladding layer in the quartz glass pipe to form an optical fiber preform; and drawing the manufactured optical fiber preform to obtain an optical fiber.

Preferably, the method may further include, after the forming of the core layer, etching an outer portion of the cladding layer that is not doped with the metal nano-particles so that at least some of the metal nano-particles are exposed to the outside.

Preferably, the method may further include coating the drawn optical fiber with a polymer having a refractive index lower than that of the cladding layer.

Preferably, the metal may be any one selected from a group consisting of gold (Au), silver (Ag), and copper (Cu).

According to another preferred embodiment of the present invention, there is provided a coreless optical fiber for an SPR sensor comprising a cladding layer, wherein the cladding layer is doped with metal nano-particles, and at least some of the metal nano-particles are exposed to the outside.

Preferably, the cladding layer may be coated with a polymer having a refractive index lower than that of the cladding layer.

Preferably, the metal may be any one selected from a group consisting of gold (Au), silver (Ag), and copper (Cu).

According to another preferred embodiment of the present invention, there is provided a method for manufacturing a coreless optical fiber for an SPR sensor, the method including:

depositing a cladding layer in a quartz glass pipe and partially sintering the deposited cladding layer;

doping the partially sintered cladding layer with metal nano-particles;

drying, sintering, and condensing the cladding layer doped with the metal nano-particles to manufacture an optical fiber preform; and drawing the manufactured optical fiber preform to obtain an optical fiber.

Preferably, the method may further include, after the drying, sintering, and condensing of the cladding layer, etching an outer portion of the cladding layer that is not doped with the metal nano-particles so that at least some of the metal nano-particles are exposed to the outside.

Preferably, the method may further include coating the drawn optical fiber with a polymer having a refractive index lower than that of the cladding layer.

Preferably, the metal may be any one selected from a group consisting of gold (Au), silver (Ag), and copper (Cu).

Advantageous Effects

According to the present invention, there is no need to perform the secondary processing processes of the optical fiber such as the polishing process, the tapering process, the grating process, and the coating process of the optical fiber for depositing the metal nano-particles on the surface of the optical fiber after manufacturing the optical fiber to thereby be used as the sensing probe, by doping the cladding layer with the metal nano-particles in the step of the optical fiber preform.

BEST MODE

In the present invention, a specific optical fiber capable of being directly used as an optical sensor probe without being subjected to a secondary processing process simultaneously with being manufactured was developed for the first time in the world as follow.

1. Optical Fiber for SPR Sensor

Figure 1:
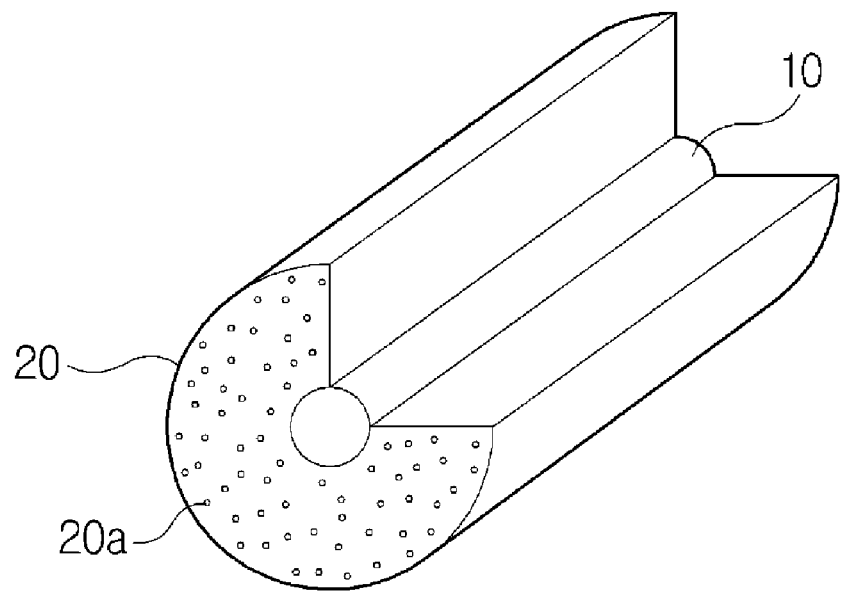
FIG. 1 is a view showing a cross-sectional structure of an optical fiber for a surface plasmon resonance (SPR) sensor according to an embodiment of the present invention.

As shown in FIG. 1, the optical fiber for an SPR sensor according to the present invention is configured to include a core layer 10 and a cladding layer 20 enclosing the core layer 10, wherein the cladding layer 20 is doped with metal nano-particles 20a, and preferably, at least some of the metal nano-particles 20a are exposed to the outside. The metal nano-particles may have a diameter selected in a range of preferably 1 to 100 nm, more preferably 1 to 10 nm.

Preferably, in the case in which the optical fiber is manufactured by a modified chemical vapor deposition (MCVD) method, an outer portion of the cladding layer 20 need to be etched so that at least some of the metal nano-particles 20a are exposed to the outside, but in the case in which the optical fiber is manufactured by a vacuum oxygen decarburization (VOD) method or a vacuum arc degassing (VAD) method, this etching may be unnecessary.

Figure 2:
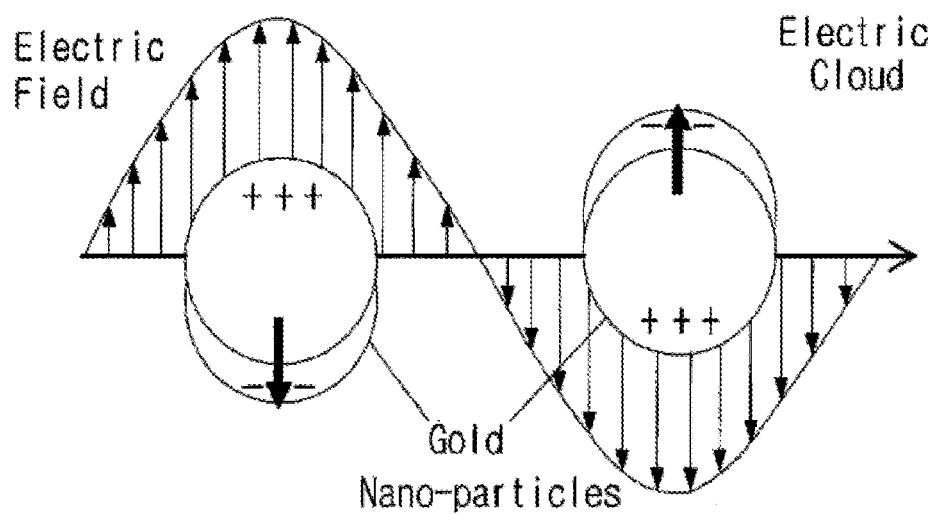
FIG. 2 is a view for schematically describing a surface plasmon resonance phenomenon by metal nano-particles contained in a cladding region of the present invention.
Figure 3:
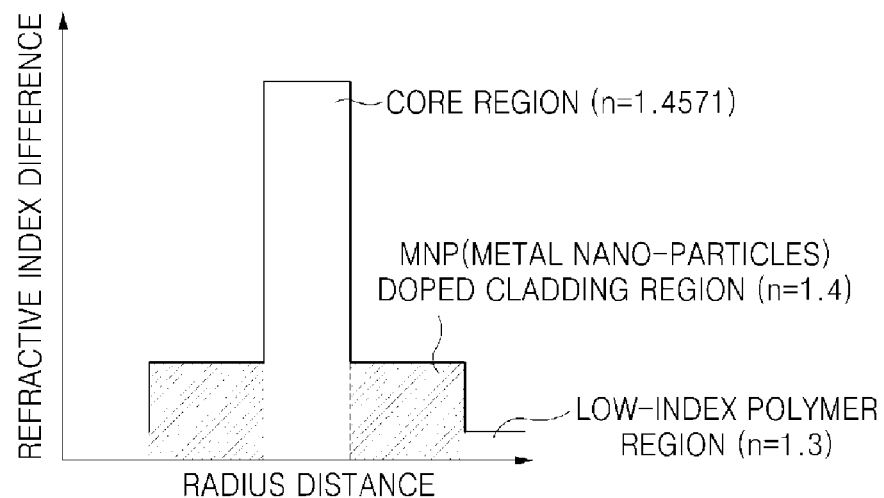
FIGS. 3 to 7 are views showing various examples of a practicable design of an optical fiber for an SPR sensor in which a cladding layer according to the embodiment of the present invention is doped with metal nano-particles.
Figure 4:
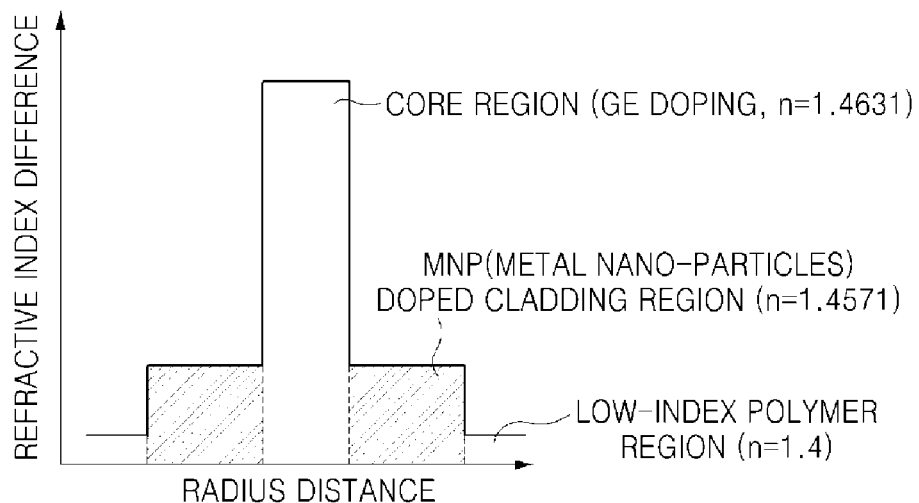
Figure 5:
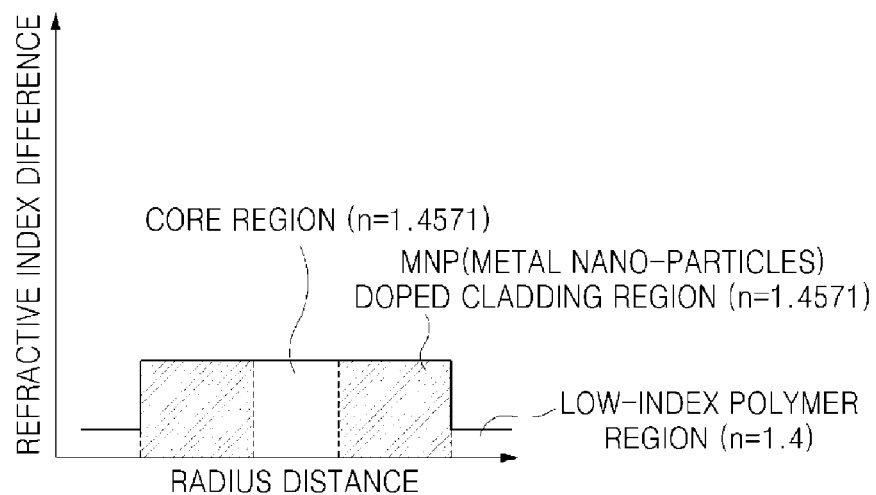
Figure 6:
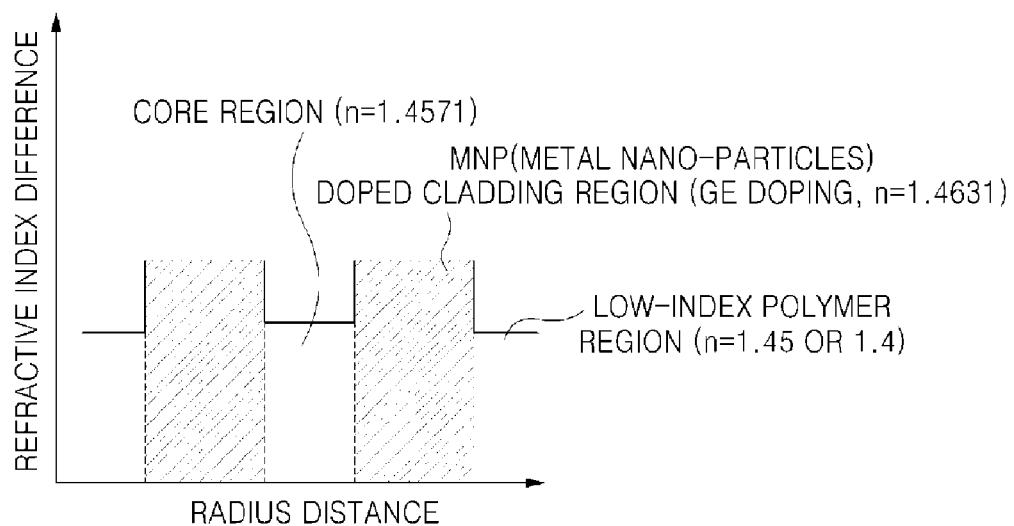
Figure 7:
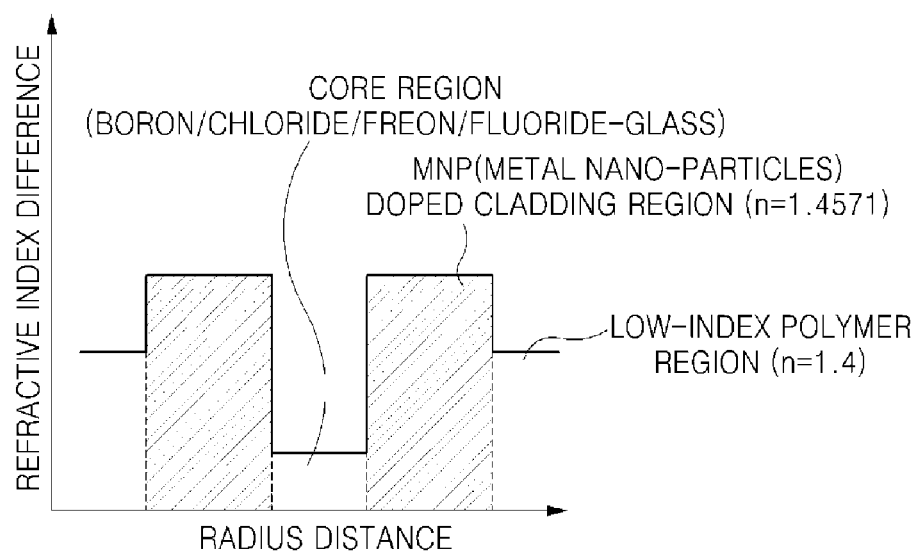

The metal nano-particles present in a cladding region of the optical fiber according to the present invention may generate localized surface plasmon resonance (LSPR) as shown in FIG. 2. The LSPR means collective oscillation of conduction band electrons propagated along an interface between a metal having a negative dielectric function ($\in$'<0) and a medium having a positive dielectric function ($\in$'>0). As a result of an interaction with an incident electromagnetic wave, the electrons are excited to thereby have properties and a form of an evanescent wave having a magnitude increased as compared to the incident light and exponentially decreased as the electrons are far from the interface in a vertical direction.

The optical fiber according to the present invention may be utilized as various sensors using properties that at least some of the metal nano-particles 20a of the cladding layer 20 are exposed to the outside and a surface plasmon frequency is changed according to the kinds of materials contacted by the exposed metal nano-particles 20a and sizes, shapes, and size distribution of the nano-particles.

That is, in the optical fiber according to the present invention, the cladding layer 20 is doped with the metal nano-particles 20a and at least some of the metal nano-particles are exposed, such that the surface plasmon resonance phenomenon is induced in the surface of the optical fiber to thereby allow the optical fiber to be utilized as a sensing probe. Therefore, the sensor may be manufactured by a simple process that does not require the post-processing of the optical fiber.

The metal used in the present invention may be preferably at least one selected from Ag, Au, Cu, Pb, Sn, Pt, Al, Sc, Ti, V, Cr, Mn, Fe, Co, Ni, Zn, Y, Zr, Nb, Mo, Tc, Ru, Rh, Pd, Cd, In, Hf, Ta, W, Re, Os, Ir, Tl, and Bi, more preferably at least one selected from Au, Ag, and Cu, and most preferably Au.

Preferably, the cladding layer may be coated with a polymer having a refractive index lower than that of the cladding layer, such that transmission efficiency of an optical signal may be increased.

In addition, a surface of the cladding layer is coated with a metal thin film having a thickness of preferably several tens nm, more preferably 10 to 100 nm. In the case in which the surface of the cladding layer is coated with the metal thin film as described above to thereby be used as the SPR sensor, the SPR effect may be further increased.

FIGS. 3 to 7 show various examples of a practicable design of an optical fiber for an SPR sensor in which a cladding layer according to the embodiment of the present invention is doped with metal nano-particles. The optical fiber for an SPR sensor may be designed by selecting a suitable example among these various examples, as needed.

These examples are provided in order to illustrate the present invention, and those skilled in the art will appreciate that various modifications, additions and substitutions are possible, without departing from the scope and spirit of the invention as disclosed in the accompanying claims.

2. Manufacturing of Optical Fiber for SPR Sensor

Figure 8:
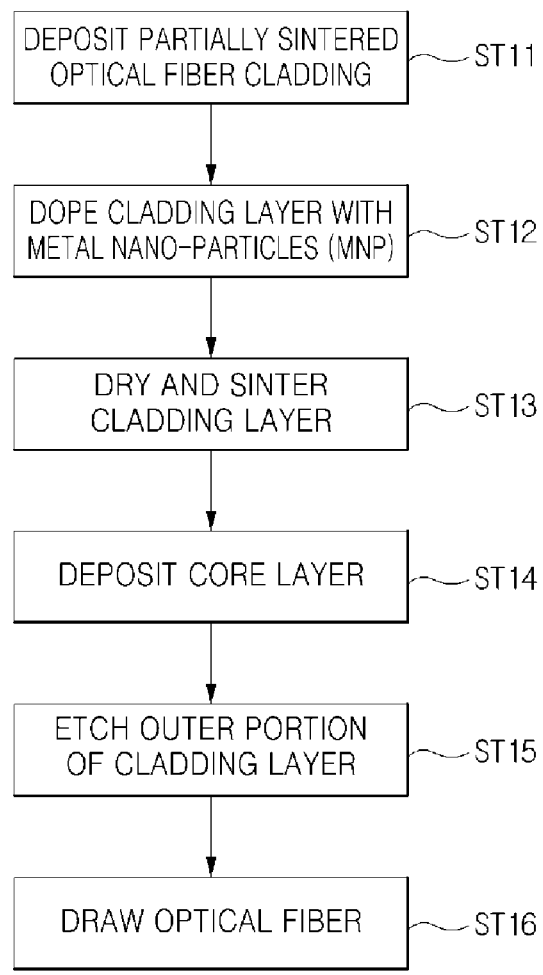
FIG. 8 is a flow chart showing a manufacturing process of the optical fiber for an SPR sensor according to the embodiment of the present invention.

An entire manufacturing process of the optical fiber for an SPR sensor according to the present invention is shown in FIG. 8.

1) Firstly, SiCl$_4$, POCl$_3$, and CF$_4$ which are mixed at a suitable ratio and oxygen are mixed with each other in a quartz glass pipe to deposit a cladding layer and then partially sinter the cladding layer (ST11).

The reason of partially sintering the cladding layer is in order to form a porous structure having a large amount of gaps between glass fine particles to allow a solution containing the metal nano-particles to easily infiltrate into the cladding layer and easily adsorbed by the cladding layer by the following solution addition method. In the case in which the sintering is not performed at all, the cladding layer may be broken down in a step of doping the metal nano-particles by the following solution addition method.

2) Then, the metal nano-particles are doped in the partially sintered porous structure of the cladding layer by the solution addition method, that is, by injecting the solution containing the metal nano-particles into the quartz glass pipe (ST12).

Figure 9A:
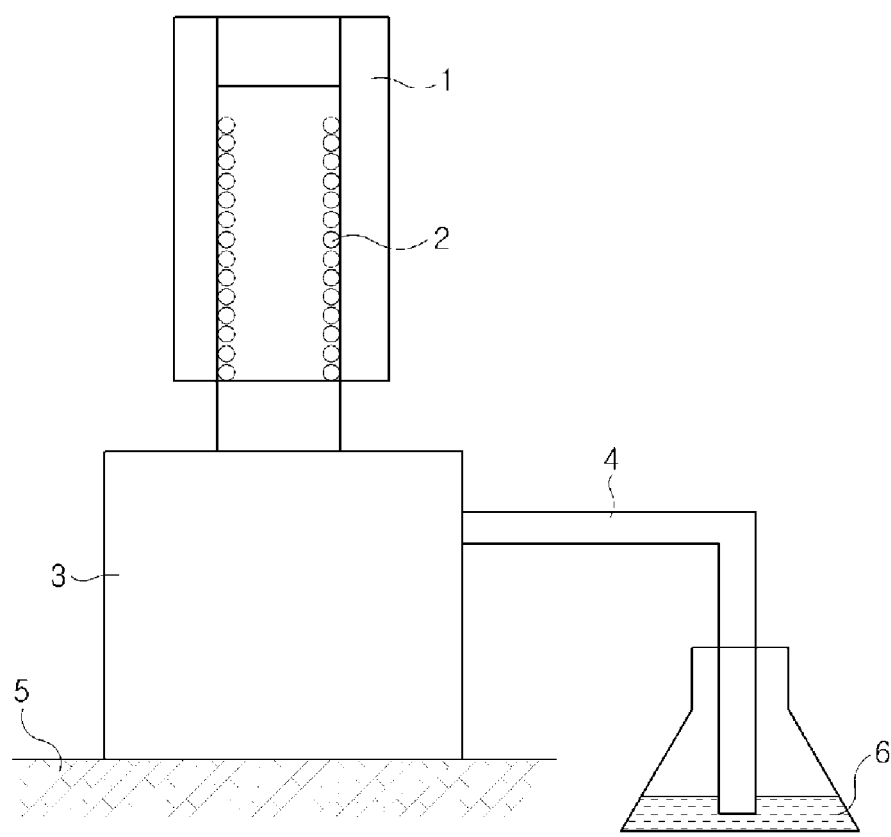
FIGS. 9A to 9C are views showing apparatus setting in various dopant addition methods used in the manufacturing process of the optical fiber for an SPR sensor according to the embodiment of the present invention.
Figure 9B:
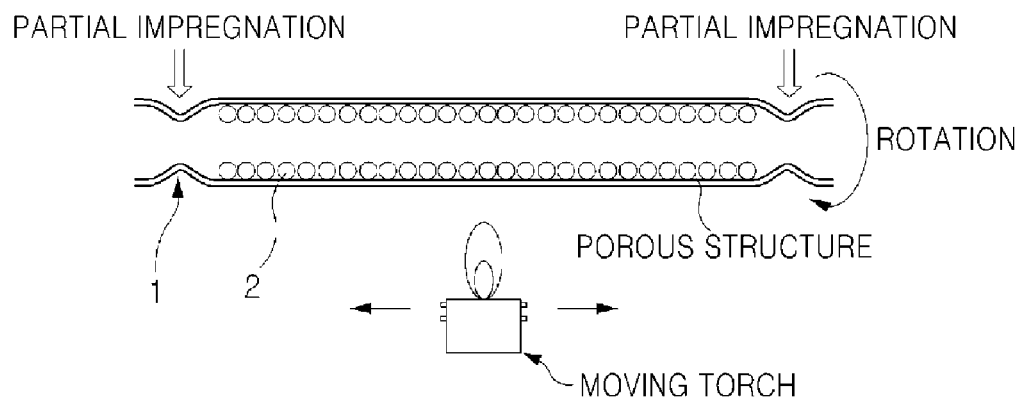
Figure 9C:
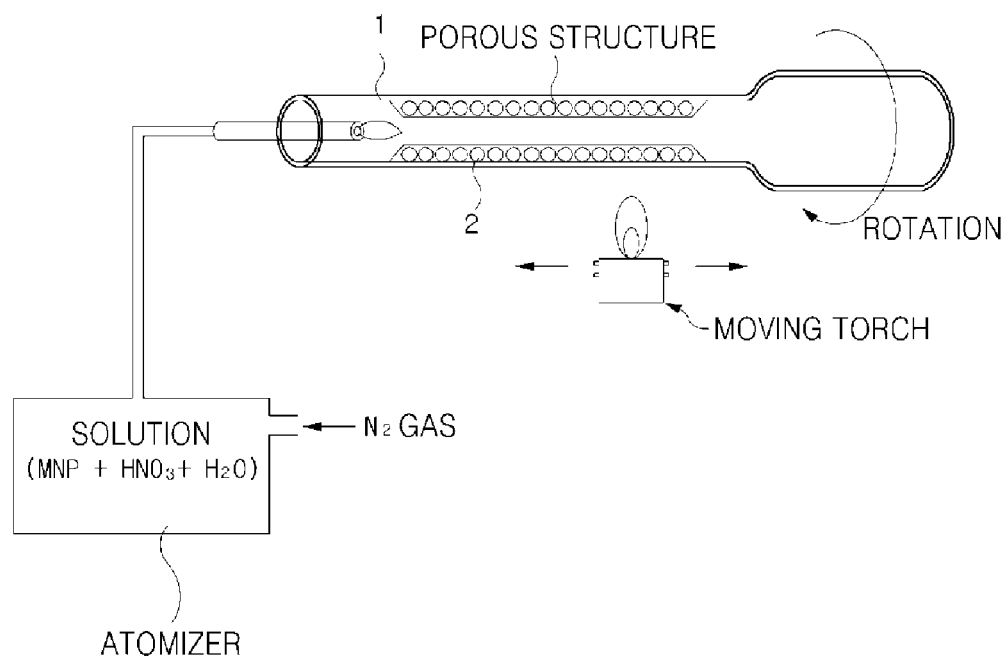

Here, the step of doping the metal nano-particles on the cladding layer is performed by a solution doping apparatus shown in FIGS. 9A to 9C.

Referring to FIG. 9A, after the cladding layer is partially sintered, a quartz glass pipe 1 in which the glass fine particles 2 that will become the cladding layer are deposited is manufactured, and this quartz glass pipe 1 on which the glass fine particles 2 are deposited is connected to a hose 4 using a connector 3 and installed so as to be vertical to the ground 5. Then, in the case in which a solution 6 containing the metal nano-particles to be contained in the cladding layer is injected using the hose 4, the solution 6 passes through the connector 3 to thereby be filled in the quartz glass pipe 1.

In this state, the solution 6 is discharged to the outside of the quartz glass pipe 1 through the hose 4 after a predetermined time so that the solution is infiltrated between soot particles. Most of the solution 6 is discharged to the outside of the quartz glass pipe 1 through the hose 4, but after the solution 6 is discharged, the solution 6 is partially adsorbed by the soot to thereby remain in the gaps between the soot particles, such that the desired metal nano-particles are doped on the cladding layer.

The doping may also be performed by a solution horizontal addition method and a solution addition method using an atomizer that are known in the art, as shown in FIGS. 9B and 9C, respectively, as well as the above-mentioned solution vertical addition method.

3) The cladding layer doped with the metal nano-particles as described above is dried and then completely sintered (ST13).

4) Thereafter, a core layer is formed in the quartz glass pipe by a jacketing process, thereby manufacturing an optical fiber preform (ST14).

5) Next, preferably, in the case in which the optical fiber preform is manufactured by the MCVD method, an outer wall of the cladding layer that is not doped with the metal nano-particles is etched so that at least some of the metal nano-particles are exposed to the outside (ST15). Through this step of etching, the cladding region in which the metal nano-particles are contained may smoothly contact external materials. Preferably, the present step may be performed using an acidic solution (for example, HF solution). Unlike this, in the case in which the optical fiber preform is manufactured by the VOD or VAD method, this step (ST15) may be unnecessary.

6) Thereafter, the optical fiber preform obtained above is drawn through a drawing process of the optical fiber at a high temperature, preferably, about 2150° C., thereby manufacturing an optical fiber including a core and a cladding having predetermined diameters (ST16). Preferably, the diameters of the core and the cladding may be 100 μm and 125 μm, respectively.

7) In addition, preferably, in order to maximize the surface plasmon resonance effect by the metal nano-particles in the drawing process of the optical fiber, the cladding layer is coated with a low-index polymer having a refractive index lower than that of the cladding layer, such that the transmission efficiency of an optical signal may be increased.

3. Coreless Optical Fiber for SPR Sensor

Figure 10:
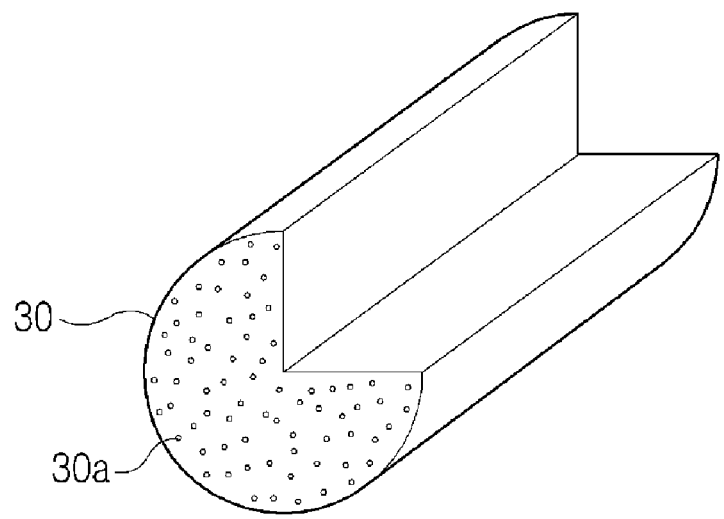
FIG. 10 is a view showing a cross-sectional structure of a coreless optical fiber for an SPR sensor according to another embodiment of the present invention.

As shown in FIG. 10, a coreless optical fiber for an SPR sensor according to the present invention may be configured of a cladding layer, wherein the cladding layer is doped with metal nano-particles, and preferably, at least some of the metal nano-particles are exposed to the outside.

That is, since other features of the coreless optical fiber for an SPR sensor according to the present invention are the same as those of the optical fiber described above in 1 except that a core is not formed at a central portion of the optical fiber, descriptions of these common features will be omitted in order to avoid an overlapped description.

Figure 11:
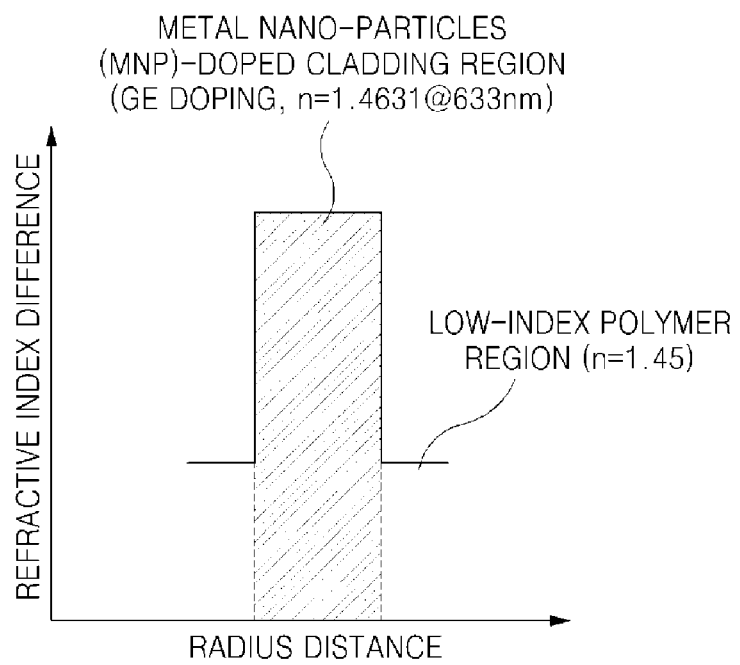
FIG. 11 is a view showing an example of a design of the coreless optical fiber for an SPR sensor in which a cladding layer according to the embodiment of the present invention is doped with metal nano-particles.
Figure 12:
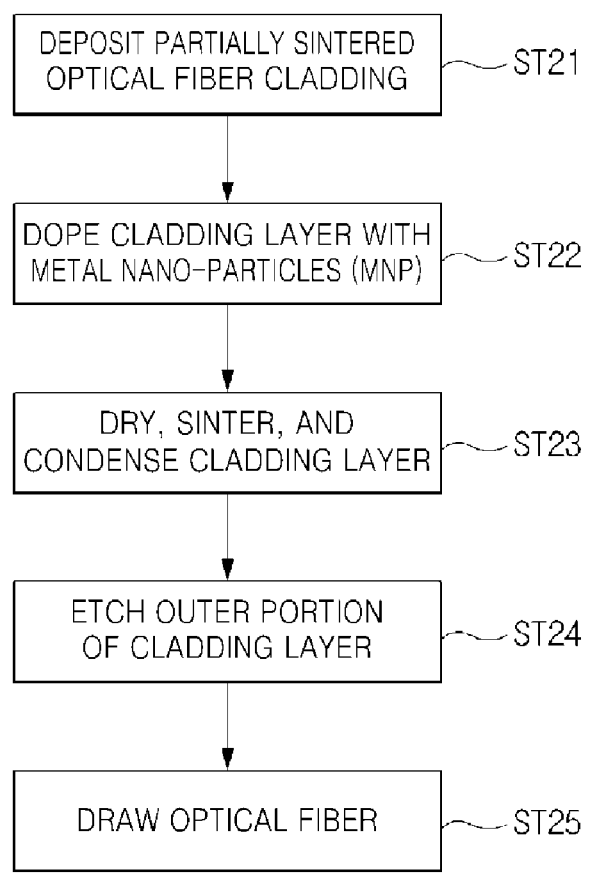
FIG. 12 is a view showing a manufacturing process of the coreless optical fiber for an SPR sensor according to the embodiment of the present invention.

FIG. 11 shows an example of a design of the coreless optical fiber for an SPR sensor in which a cladding layer according to the embodiment of the present invention is doped with metal nano-particles.

4. Manufacturing of Coreless Optical Fiber for SPR Sensor

As shown in FIG. 11, the coreless optical fiber for an SPR sensor according to the present invention may include a step of depositing a partially sintered optical fiber cladding (ST21), a step of doping metal nano-particles (MNP) on the cladding (ST22), a step of drying, sintering, and condensing the cladding layer (ST23), a step of etching an outer portion of the cladding layer (ST24), and a step of drawing the optical fiber (ST25).

That is, since in the manufacturing process of the coreless optical fiber for an SPR sensor according to the present invention, other steps are the same as those in the manufacturing process of the optical fiber described in 2 except that the step of drying, sintering, and condensing the cladding layer (ST23) is included instead of the step of drying and sintering the cladding layer (ST13) and the step of depositing the core layer (ST14), descriptions of these common steps will be omitted in order to avoid an overlapped description.

EXAMPLE

A specific optical fiber containing AU nano-particles in an optical fiber cladding region was manufactured using a modified chemical vapor deposition (MCVD) process and a drawing process at a high temperature. In order to solid-solubilize the Au nano-particles in the optical fiber cladding region, after a partially sintered optical fiber cladding (core) was deposited through the MCVD process, the doping was performed using a solution (0.025 mole) prepared using $Au(OH)_3$ (Aldrich Chem. Co. Inc., 99.9%) and $HNO_3$ solution (Junsei Co., 70%). These procedures were commonly applied to the following Examples 1 and 2.

Example 1

Manufacturing of Optical Fiber for SPR Sensor

Then, after an optical fiber cladding containing Au nano-particles and having a refractive index of 1.4571 (at 633 nm) was manufactured through a drying process and a sintering process, a special optical fiber preform in which the Au nano-particles were solid-solubilized in the cladding region was manufactured by a jacketing process using an optical fiber bar having a refractive index of 1.4629 (at 633 nm). Further, in order to induce a surface plasmon resonance phenomenon in a surface of the optical fiber, a silica glass outer wall of the special optical fiber preform was etched using an HF solution. After the cladding region in which the Au nano-particles were contained was formed as the outermost layer for smooth contact with an external material through the etching process, a special optical fiber including a core and a cladding having diameters of 100 µm and 125 µm, respectively, was developed through a drawing process of the optical fiber at a high temperature of 2150° C. Further, in order to maximize the surface plasmon resonance effect by the Au nano-particles during the drawing process of the optical fiber, transmission efficiency of an optical signal was increased through low-index polymer coating.

Example 2

Manufacturing of Coreless Optical Fiber for SPR Sensor

Meanwhile, an optical fiber preform bar containing Au nano-particles and having a refractive index of 1.4571 (at 633 nm) was manufactured through a drying process, a sintering process, and a condensing process. In order to induce an actual surface plasmon resonance phenomenon in a surface of a special optical fiber to be developed using the manufactured special optical fiber preform bar in which the Au nano-particles were solid-solubilized, a silica glass outer wall of the manufactured special optical fiber preform was etched using a HF solution. After the region in which the Au nano-particles were contained was allowed to become the outermost layer for smooth contact with an external material through the etching process, a special coreless optical fiber of which a diameter was 125 µm, and a diameter of the coating was 250 µm was developed using the manufactured special optical fiber preform bar through a drawing process of the optical fiber at a high temperature of 2150° C. and a coating process of the optical fiber using a low-index polymer.

Figure 13:
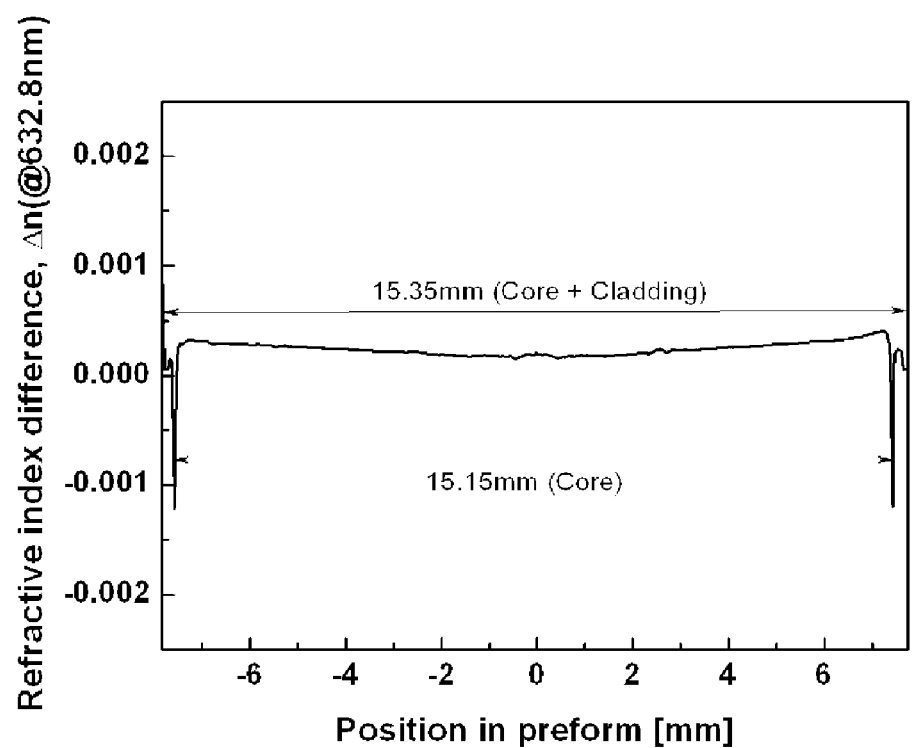
FIG. 13 shows refractive index distribution of a special optical fiber preform in which Au nano-particles are contained in a cladding region of an optical fiber actually developed according to the present invention.

FIG. 13 shows refractive index distribution of a special optical fiber preform in which the Au nano-particles are contained in the cladding region of the optical fiber actually developed according to the present invention before and after etching.

INDUSTRIAL AVAILABILITY

According to the present invention, a coreless optical fiber for an SPR sensor may also be manufactured by applying a conventional method for manufacturing glass such as a glass melting method, a sol-gel method, or the like in addition to the above-mentioned method.

The invention claimed is:

1. An optical fiber for a surface plasmon resonance (SPR) sensor, the optical fiber comprising:
    a core layer;
    a cladding layer enclosing the core layer,
    wherein the cladding layer includes doped metal nano-particles,
    at least some of the metal nano-particles are exposed on an outer surface of the cladding layer, and
    the cladding layer comprises a metal film coating on a surface of the cladding layer, the metal film contacts a surface of the metal nano-particles exposed on the outer surface of the cladding layer, wherein the coated metal film is configured to be operated as the SPR sensor.

2. The optical fiber of claim 1, further comprising:
    a coating on the cladding layer, the coating comprises a polymer having a refractive index lower than a refractive index of the cladding layer.

3. The optical fiber of claim 1, wherein the metal includes at least one metal selected from the group consisting of gold (Au), silver (Ag), or copper (Cu).

4. A method for manufacturing an optical fiber for a surface plasmon resonance (SPR) sensor, the method comprising:
    depositing a cladding layer, the cladding layer comprising $SiCl_4$, $POCl_3$, $CF_4$ and oxygen, in a quartz glass pipe and partially sintering the deposited cladding layer;
    doping the partially sintered cladding layer with metal nano-particles;
    drying and sintering the cladding layer doped with the metal nano-particles;
    forming a core layer on the cladding layer in the quartz glass pipe to manufacture an optical fiber preform;
    etching an outer portion of the cladding layer that is not doped with the metal nano-particles so that at least some of the metal nano-particles are exposed on an outer surface of the cladding layer;
    coating a surface of the cladding layer with a metal film so that the metal film contacts a surface of the metal nano-particles exposed on the outer surface of the cladding layer, wherein the coated metal film is configured to be operated as the SPR sensor; and
    drawing the manufactured optical fiber preform to obtain an optical fiber.

5. The method of claim 4, further comprising:
    coating the drawn optical fiber with a polymer having a refractive index lower than a refractive index of the cladding layer.

6. The method of claim 4, wherein the metal includes at least one metal selected from the group consisting of gold (Au), silver (Ag), or copper (Cu).

7. The method of claim 4, further comprising:
    coating a metal film on a surface of the cladding layer, wherein the coated metal film is configured to be operated as the SPR sensor.

8. The method of claim 4, wherein said forming comprises forming the core layer on the cladding layer in the quartz glass pipe by using an outside vapor deposition (VOD) method.

9. The method of claim 4, wherein said forming comprises forming the core layer on the cladding layer in the quartz glass pipe by using a vapor axial deposition (VAD) method.

10. A coreless optical fiber for a surface plasmon resonance (SPR) sensor, the coreless optical fiber comprising:
    a cladding layer, wherein the cladding layer includes doped metal nano-particles; wherein at least some of the metal nano-particles are exposed on an outer surface of the cladding layer, and
    wherein the cladding layer comprises a metal film coating on a surface of the cladding layer, the metal film contacts a surface of the metal nano-particles exposed on the outer surface of the cladding layer, and the coated metal film is configured to be operated as the SPR sensor.

11. The coreless optical fiber claim 10, further comprising:
    a coating on the cladding layer, the coating comprises a polymer having a refractive index lower than a refractive index of the cladding layer.

12. The coreless optical fiber of claim 10, wherein the metal includes metal at least one selected from the group consisting of gold (Au), silver (Ag), or copper (Cu).

13. A method for manufacturing a coreless optical fiber for a surface plasmon resonance (SPR) sensor, the method comprising:

depositing a cladding layer, the cladding layer comprising $SiCl_4$, $POCl_3$, $CF_4$ and oxygen, in a quartz glass pipe and partially sintering the deposited cladding layer;

doping the partially sintered cladding layer with metal nano-particles;

drying, sintering, and condensing the cladding layer doped with the metal nano-particles to manufacture an optical fiber preform;

etching an outer portion of the cladding layer that is not doped with the metal nano-particles so that at least some of the metal nano-particles are exposed on an outer surface of the cladding layer;

coating a surface of the cladding layer with a metal film so that the metal film contacts a surface of the metal nano-particles exposed on the outer surface of the cladding layer, wherein the coated metal film is configured to be operated as the SPR sensor; and drawing the manufactured optical fiber preform to obtain an optical fiber.

14. The method of claim 13, further comprising:

coating the drawn optical fiber with a polymer having a refractive index lower than a refractive index of the cladding layer.

15. The method of claim 13, wherein the metal includes at least one metal selected from the group consisting of gold (Au), silver (Ag), or copper (Cu).

16. The method of claim 13, further comprising:

coating a metal film on a surface of the cladding layer, wherein the coated metal film is configured to be operated as the SPR sensor.

* * * * *